United States Patent [19]
Daikuzono

[11] Patent Number: 5,209,748
[45] Date of Patent: May 11, 1993

[54] LASER LIGHT IRRADIATION APPARATUS
[75] Inventor: Norio Daikuzono, Chiba, Japan
[73] Assignee: S.L.T. Japan Co., Ltd., Tokyo, Japan
[21] Appl. No.: 899,043
[22] Filed: Jun. 16, 1992

Related U.S. Application Data
[63] Continuation of Ser. No. 568,124, Aug. 16, 1990, abandoned.

[30] Foreign Application Priority Data
Aug. 24, 1989 [JP] Japan ............................. 1-217869

[51] Int. Cl.$^5$ ............................................. A61B 17/36
[52] U.S. Cl. .......................................... 606/16; 606/7; 606/15; 606/17
[58] Field of Search .......................... 606/2, 7, 10–17; 128/395, 396, 397, 398

[56] References Cited
U.S. PATENT DOCUMENTS

| | | |
|---|---|---|
| 4,126,136 | 11/1978 | Auth et al. |
| 4,233,493 | 11/1980 | Nath |
| 4,322,164 | 3/1982 | Shaw et al. .......................... 356/243 |
| 4,648,892 | 3/1987 | Kittrell et al. |
| 4,649,151 | 3/1987 | Dougherty et al. |
| 4,660,925 | 4/1987 | McCaughan, Jr. .............. 350/96.15 |
| 4,669,467 | 6/1987 | Willett et al. |
| 4,693,556 | 9/1987 | McCaughan, Jr. ................. 350/320 |
| 4,736,743 | 4/1988 | Daikuzono |
| 4,773,579 | 9/1988 | Unuma |
| 4,799,479 | 1/1989 | Spears |
| 4,832,979 | 5/1989 | Hoshino |
| 4,848,339 | 7/1989 | Rink et al. |
| 4,850,351 | 7/1989 | Herman et al. |
| 4,860,743 | 8/1989 | Abela |
| 4,862,886 | 9/1989 | Clarke et al. ............................ 606/7 |
| 4,866,168 | 9/1989 | Dougherty et al. |
| 4,994,060 | 2/1991 | Rink et al. .............................. 606/28 |
| 5,054,867 | 10/1991 | Wagnieres et al. ..................... 385/31 |
| 5,059,191 | 10/1991 | Beyer et al. .............................. 606/2 |

FOREIGN PATENT DOCUMENTS

| | | |
|---|---|---|
| 214712 | 3/1987 | European Pat. Off. |
| 61-181455 | 8/1986 | Japan |
| 62-34553 | 2/1987 | Japan |
| 63-216579 | 9/1988 | Japan |
| 2-34161 | 2/1990 | Japan |
| 2-39003 | 2/1990 | Japan |
| 2-98373 | 4/1990 | Japan |
| 1-135370 | 5/1992 | Japan |
| 2185188 | 12/1986 | United Kingdom |

OTHER PUBLICATIONS
"Photodynamic Therapy of Early Cancer . . . " Wagnieres et al., SPIE Institute Series, Jun. 1990.
Nobori et al., "The Application of YAG Laser to Hyperthermia," *Bulletin of the Japan Society of Laser Medicine*, vol. 6, No. 3, Jan. 1986, pp. 71–76.
Suzuki et al., "Endoscopic Local Hyperthermia with Nd-YAG Laser-Experimental Study and Development of Computed Thermo-System," *Bulletin of the Japan Society of Laser Medicine*, vol. 6, No. 3, Jan. 1986, pp. 347–350.
Mashiko et al., "Basic Study on Photochemical Effect of Pheophorbide as Irradiated by Nd:YAG Laser Light," *Bulletin of the Japan Society of Laser Medicine*, vol. 6, No. 3, Jan. 1986. pp. 113–116.
Dougherty et al., "Photoradiation Therapy for the Treatment of Malignant Tumors," *Cancer Research*, vol. 38, (Aug. 1978), pp. 2628–2635.

*Primary Examiner*—Peter A. Aschenbrenner
*Attorney, Agent, or Firm*—Lowe, Price, LeBlanc & Becker

[57] ABSTRACT
A laser light irradiation apparatus used for medical treatment of tissues. According to a preferred embodiment, the apparatus comprises a probe, an optical fiber feeding laser light into the probe and a lead wire for detecting a temperature being inserted through and projecting from the probe. Then, the probe contains laser light scattering particles for uniform irradiation of the laser light against the tissues. Further, the probe is fabricated from a laser light tramissive synthetic material, and the fore end of a core of the optical fiber and the inserting part of the lead wire are in the synthetic material of the probe for easy molding for this apparatus.

13 Claims, 4 Drawing Sheets

LASER LIGHT IRRADIATION APPARATUS

This application is a continuation of application Ser. No. 07/568,124 filed Aug. 16, 1990, now abandoned.

BACKGROUND OF THE INVENTION

1. Field of the Invention

This invention relates to a laser light irradiation apparatus, which irradiates laser light to living tissues of an animal such as a human body to permit an incision, vaporization of the living tissues or a thermal therapy and, more particularly, to a laser light irradiation apparatus by which a thermal therapy can be carried out efficiently for cancer tissues and the like while the penetrating member of the laser light irradiation apparatus is brought into contact with the surface of the living tissues directly or through the intermediary of a surface layer on the penetrating member.

2. Prior Art

Medical treatments such as incisions of living tissues of animal organisms by irradiation with laser light are conspicuous due to the ability of hemostasis.

It had been the conventional method that the laser light was irradiated from the fore end of an optical fiber which is held out of contact with the living tissues. This method, however, causes severe damage to the fore end portion of the optical fiber. Therefore, a method which has been utilized lately is as follows;

First, laser light is transmitted into an optical fiber, whose fore end portion is located adjacent to the treated living tissues. Next, the laser light fed out from the fore end of the optical fiber is applied to an emitting probe, which can be held in contact or out of contact with the living tissues. Then, the laser light passes through the probe and is emitted from the surface of the probe for irradiating against the tissues. In this case, it is preferred that the probe be brought into contact with the living tissues (hereafter "living tissue" is sometimes expressed by "tissue" only).

The Applicant developed many kinds of contact probes which are utilized for various purposes.

Further, lately, localized thermal therapy is drawing special attention as a carcinostatic therapy. According to this method, cancer tissues are destroyed by keeping the cancer tissues at a temperature of about 42°–44° C. for 10-25 minutes by irradiation with laser light. The effectiveness of this method has been reported by the inventors in the Bulletin of Japan Society of Laser Medicine, Vol. 6, No. 3 (January 1986), pp. 71–76 and 347-350.

On the other hand, considerable attention has been paid to laser-chemical therapies including the method reported in 1987 by Dougherty et al of the United States. According to this method, 48 hours after an intravenous injection of a hematoporphyrin derivative (HpD), weak laser light such as argon laser or argon pigment laser is irradiated against a target area of the treatment. Whereupon oxygen of the primary term which as a strong carcinostatic action is produced by HpD. Since then, there have been published various reports in this regard, including the one in the Bulletin of Japan Society of Laser Medicine, Vol. 6, No. 3 (January 1986), pp. 113-116. In this connection, it has also been known in the art to use "pheophobide a" as a photo-reactant. Further, recently, YAG laser has been put into use as a laser light source.

In the above mentioned medical treatment, it is important that the laser light is irradiated uniformly for the cancer tissues and, in case of the thermal therapy, it is particularly important that the cancer tissues are heated uniformly.

However, it is very difficult to irradiate the laser light uniformly and it is further difficult to irradiate against a broad target area. Therefore, a following method should be carried out;

The laser light is repeated to be irradiated against each small part of the target area separately so that the whole target area can be irradiated. Accordingly, it takes a long time to perform the medical operation.

Under these circumstances, laser light irradiation apparatuses having a plural number of laser light emitters or probes were studied. With the apparatus of this type, the laser light emitted from the probes is irradiated simultaneously against the tissues. Such laser light irradiation apparatus was shown also by Applicant in Japanese Patent Application No. 62-50723.

It is sure that the laser light can be irradiated against the tissues uniformly to some degree with these apparatuses. However, uniformity is not enough. On the other hand, the plural number of laser light conduction passages and probes, and a controller for the passages and the process are necessary in these apparatuses, therefore increasing cost.

SUMMARY OF THE INVENTION

It is therefore a main object of the present invention to provide an inexpensive laser light irradiation apparatus by which laser light can be irradiated against living tissues uniformly.

In order to solve the above mentioned problems, a laser light irradiation apparatus of the present invention comprises a laser light emitting member, which contains laser light scattering particles and which is fabricated from a laser light transmissive synthetic material, and at least one laser light transmitting member, through which laser light goes so as to be fed into the penetrating member.

In case of heating the tissues efficiently, a lead wire detecting a temperature should be brought into contact with the treated tissues for controlling the temperature. Therefore, for heating the tissues, a laser light irradiation apparatus preferably comprises the laser light emitting member, which has the laser light scattering particles and which is fabricated from the laser light transmissive synthetic material, at least one laser light transmitting member, through which the laser light goes so as to be fed into the emitting member. A lead wire detecting the temperature is inserted through the penetrating member so as to project from the external surface of the fore end portion of the emitting member. A part of the lead wire embedded in the synthetic material of the penetrating member.

Now, comparing the prior art, the advantages of the present invention will be described.

Almost all of the contact probes which had been invented by the Applicant, are fabricated from a ceramic material such as sapphire and the like. In order to scatter laser light with these probes, only the following method had been found; the surface of the probe should be roughened or a laser light scattering surface layer should be provided on the surface of the probe.

On the other hand, since the probe fabricated from the ceramic material is excellent in heat resistance, the probe can be used effectively when heat resistance is required. However, when the tissues are heated as described above, a high power level of the laser light is not required, and the probe operates sufficiently with low power level of the laser light.

As the result of research, Applicant has found a synthetic material to be used as the emitting member in the probe of the present invention. Then, by fabricating the synthetic material probe to contain laser light scattering particles and to have a predetermined shape, the laser light fed into the probe is scattered by the scattering particles in the probe. Therefore, the laser light is emitted in various directions from the surface of the probe. This produces a large area of laser light irradiation. Further, since the probe is fabricated from the synthetic material, the probe also has an advantage that it can be formed in many suitable shapes according to the usage of the probe.

The lead wire detecting the temperature in the tissues is necessary for controlling the temperature for a suitable medical treatment. Therefore, the probe can be formed from the synthetic material so that the lead wire detecting the temperature such as the lead wire having a thermocouple at its fore end can be inserted through the probe. In this case, the temperature is required to be detected at a position, which exists inside of the tissues and which is adjacent to the fore end of the probe being brought into contact with the surface of the tissues. Then, according to the present invention, detecting the temperature can be carried out precisely due to the suitable location of the lead wire. However, in the prior art, the temperature at the above mentioned position can not be detected for the following reasons:

In the prior art, it has been known that the lead wire is provided separately with a probe or a balloon. Therefore, the thermocouple attached to the fore end of the lead wire is set to be inserted into the tissues at the side part of the probe. That is to say, the thermocouple cannot be set the above mentioned position in the tissues due to the unsuitable location of the lead wire. Accordingly, it is impossible to detect the temperature at the above mentioned precise position. Alternatively, it has been known that the lead wire is passed around and attached from the side surface to the tip end of the probe and the fore end of the lead wire is attached to the tip end of the probe. By this method, the temperature at a point on the surface of the tissues adjacent to the fore end of the contacted probe can be detected. However, the detected temperature is that of the surface of the tissues and is not that of the inside of the tissues. As a result, by the conventional methods, it is impossible to detect the temperature at the precise position.

However, in the present invention, since the emitting member or the probe is fabricated from the synthetic material, the probe can be formed so that the lead wire can be inserted through and buried in the synthetic material of the probe. The lead wire has the thermocouple at its fore end. Further, since the fore end of the lead wire projects from the external surface of the fore end portion of the probe, when the probe is brought into contact with the tissues, the fore end of the lead wire is inserted into the tissues together with the fore end of the probe. Accordingly, by the apparatus of the present invention, the temperature at the precise position, which is adjacent to the fore end of the contacted probe and inside of the tissues, can be detected. That is to say, the probe is excellent in temperature control for heating the tissues.

As a result, by the above mentioned laser light irradiation apparatus of the present invention, the emitting member can be fabricated to be a desired shape easily, decrease in cost for fabricating the apparatus is attained and the lead wire detecting the temperature can be placed so as to be suitable for each medical treatment. Further, the laser light can be uniformly irradiated against the living tissues.

Further objects and advantages of the present invention will be apparent from the following description, reference being made to the accompanying drawings wherein preferred embodiments of the present invention are clearly shown.

DESCRIPTION OF THE PREFERRED EMBODIMENT

Figure 1:
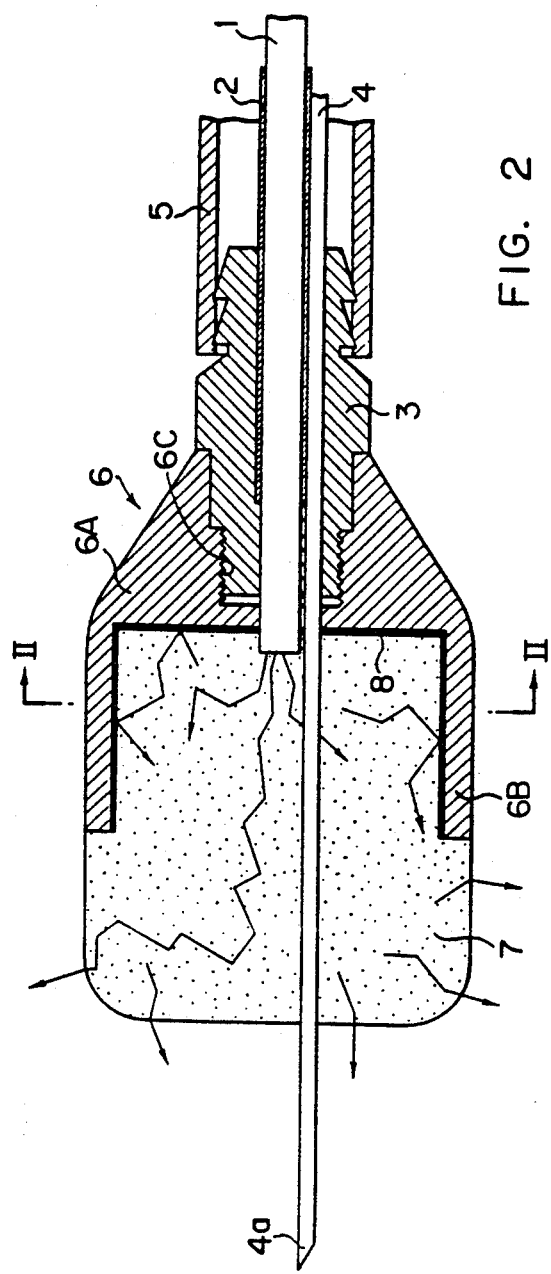
FIG. 1 is a longitudinal sectional view of an important part of an irradiation apparatus in a first embodiment related to the present invention.
Figure 2:
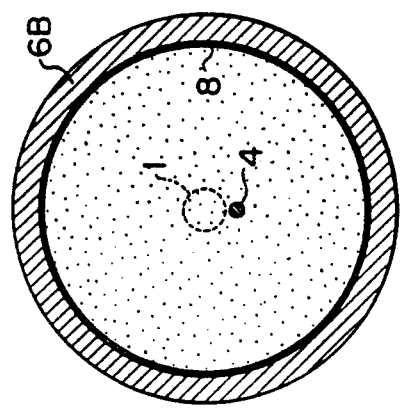
FIG. 2 is a sectional view taken on line II—II of FIG. 1.

Now, the present invention is described more particularly with regard to several embodiments shown in the drawings.

FIG. 1 shows a first embodiment. An optical fiber 1, which serves as a laser light transmitting member, is surrounded by a sheath tube 2, which is fabricated from the resin of tetrafluorethylene and the like. The fore end portion of the optical fiber 1 is inserted through a nipple 3, which is fabricated from a synthetic material such as polyethylene and the like. A lead wire 4 detecting a temperature having a thermocouple 4a at its fore end is provided alongside the optical fiber 1 and is also inserted through the nipple 3.

A flexible protective tube 5, which is fabricated from the resin of tetrafluorethylene and the like, is connected to the back end of the nipple 3. The back end of the optical fiber 1 is optically connected to a laser light generator (not shown). The lead wire 4 for detecting temperature is connected to a temperature measuring unit (not shown). Then, according to the result of detecting the temperature, the power level of the laser light, which is fed into the optical fiber 1 from the laser light generator, should be controlled. This controlling is carried out by, for example, adjusting a timer switch, which is provided between the laser light generator and the back end of the optical fiber 1.

On the other hand, the fore end portion of the nipple 3 is connected to a holder 6 by means of a screw. The holder 6 at its fore end portion, holds a probe 7 as a laser light emitting member.

The holder 6 comprises a body 6A, which is tapered toward its back end, and a sleeve-like connector 6B, which has a hollow shape and which is projected from the body 6A. The screw of the nipple 3 is adapted to mate with a connecting screw hole 6C of the holder 6 for connection. The optical fiber 1 and the lead wire 4 for detecting the temperature are inserted through the body 6A. The probe 7 composes a substantially cylindrical part with a fore end circumference, which is rounded off, and another cylindrical part at the back side of the substantially cylindrical part having a radius reduced by the thickness of the sleeve-like connector 6B. The smaller cylindrical part of the probe 7 is fitted into the sleeve-like connector 6B, and might be fixed integrally thereto by using an adhesive between the mating surfaces, i.e. a circumferential bottom face of the larger cylindrical part of the probe 7 and the top circumferential face of the sleeve-like connector 6B, for high attachment strength in fixing.

A laser light reflective layer 8 is formed on the mating surfaces of the probe 7 and the holder 6, in this embodiment on the circular front face of the body 6A and the internal side face of the sleeve-like connector 6B. Although the reflective layer 8 is preferably gold plated to give high heat resistance, it might be aluminum plated and the like, in view of the material of the layer. For forming the layer, vapor-deposit as well as plating can be used.

Further, the fore end portion of the optical fiber 1 is inserted to be buried in the synthetic material of the probe 7 and the fore end of the core of the optical fiber 1 is contacted with the synthetic material of the probe 7 directly without any gap. The fore end portion of the lead wire 4 detecting the temperature is inserted through the probe 7 so as to project from the external surface of the fore end portion of the probe 7 and has a sharpened tip end for inserting into the tissues easily.

The probe of the present invention contains laser light scattering particles and is fabricated from the laser light transmissible synthetic material. The material is synthetic resin such as silicone resin, acrylic resin (more preferably, methyl methacrylate resin), carbonate resin, polyamide resin, polyethylene resin, urethane resin, polyester resin and the like, more preferably, thermoplastic synthetic resin. For the scattering particles, the material, which has a larger refractive index for the laser light than that of the above mentioned synthetic material of the probe, is used, for example, a natural or artificial material such as diamond, sapphire, quartz material, single crystal zirconium oxide, laser light transmissible synthetic resin having heat resistance (it is needless to say that it is different from the above mentioned synthetic resin material of the probe), laser light reflective metal (such as gold, aluminum and the like), and these particles on whose surface the above mentioned laser light reflective metal is coated to be a compound material.

On the other hand, if desired, when the probe contains laser light absorbing particles such as carbon, graphite, iron oxide, manganese dioxide and the like together with the scattering particles, the laser light is impinged on the absorbing particles to generate heat energy while the laser light is scattered in the probe to be emitted from the probe.

The probe 7 of the present invention is made by molding to a desired shape a synthetic material which is in a molten state and into which the scattering particles are dispersed. In the present invention, the fore end portion of the optical fiber 1 is buried or embedded in the synthetic material of the probe 7, as shown in FIG. 1, and the middle part of the lead wire 4 detecting the temperature is buried in the synthetic material of the probe 7 so as to be fixed integrally to the probe 7. Accordingly, for fabricating this apparatus, for example, the holder 6 is made easily by molding from one mold to which the material is poured, while the optical fiber 1 and the lead wire 4 are projected from the body 6A of the holder 6.

The laser light irradiation apparatus of the type described above in the present invention is used, for example, in the following manner. The laser light is generated from the laser light generator, while the apparatus connected to an endoscope is inserted to a treated target area in a human body. The laser light from the laser light generator is applied to the back end of the optical fiber 1 and is transmitted therein to be emitted from the fore end of the optical fiber 1. Then, the emitted laser light is applied to the probe 7 directly and passes therethrough to be emitted from its external surface. As the laser light passes through probe 7, the light will be refracted repeatedly on the scattering particles contained in the material of probe 7. Therefore, as shown in FIG. 1, the laser light, after being repeatedly refracted, is emitted from the external surface of the probe 7 uniformly against the tissues. As shown in FIG. 1, the laser light reaching the internal surface of the holder 6 is reflected on the reflection layer 8. Therefore, the metal holder 6 is prevented from being heated and from being damaged. Also, the reflected laser light is brought forward.

Figure 3:
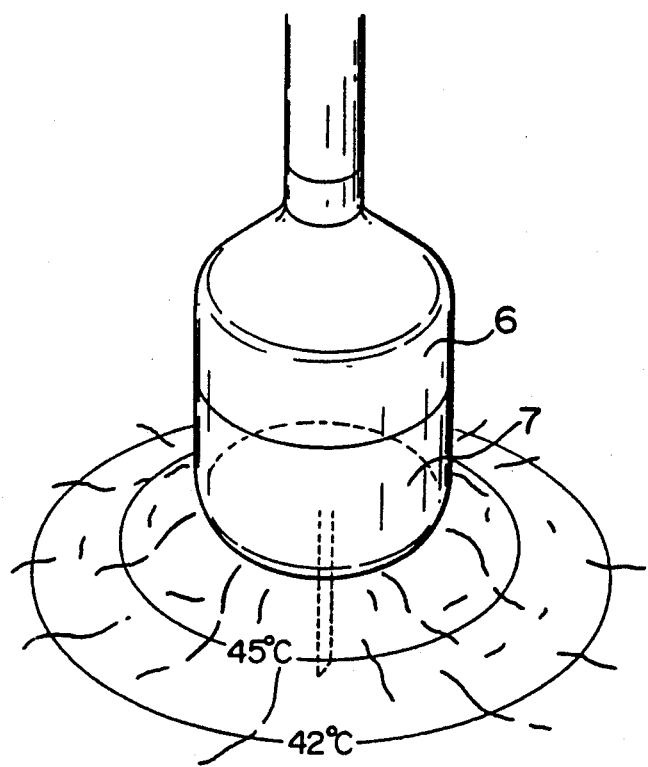
FIG. 3 is a perspective illustration showing an embodiment of local thermal therapy for cancer tissues with the irradiation apparatus of the first embodiment and the temperature distribution diagram with this apparatus.

FIG. 3 shows an embodiment where cancer tissues M are treated by a local thermal therapy with the probe 7 of the first embodiment. In this therapy, while the external surface of the fore end of the probe 7 is brought into contact with the cancer tissues M, the fore end portion of the lead wire 4 detecting the temperature, which is projected from the external surface of the fore end portion of the probe 7, is inserted into the tissues M. Then, the temperature of the tissues M is detected with the thermocouple 4a for controlling the power level of the laser light fed into the optical fiber 1; in other words, the power level of the laser light emitted from the external surface of the probe 7, as described before. Then, the cancer tissues M are destroyed by keeping the tissues M at a temperature of about 42°-44° C.

On the other hand, the laser light is irradiated against also the lead wire 4 detecting the temperature in the probe 7. Therefore, in order to prevent the lead wire 4 from being heated and from being damaged, the wire 4 is preferably coated with a laser light reflecting layer, such as a gold plated layer and a titanium coating layer.

Figure 4:
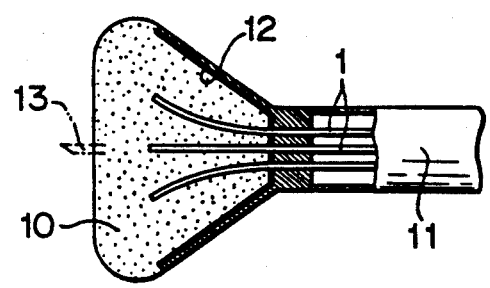
FIG. 4 is a longitudinal sectional view of an important part of an irradiation apparatus in a second embodiment.
Figure 5:
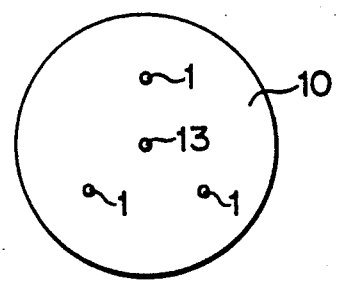
FIG. 5 is a left side view of the apparatus of FIG. 4.

FIGS. 4 and 5 show the second embodiment. The side face of a probe 10 is tapered toward the back end of the probe 10 to form a substantially truncated cone shape. Plural optical fibers 1 are provided in the probe 10, while the fore ends of the optical fibers 1 are buried in the synthetic material of the probe 10. In this embodiment, three optical fibers 1 are provided and fibers 1 are deflected toward the circumference of the fore end portion of the probe 10 to spread apart form each other from the back end of the probe 10. In a side view, the three fore ends of the fibers 1 are disposed circumferentially with the same angular space of 120°, as shown in FIG. 5. A holder 11 held by a medical operator directly has a fore end part, which is tapered towards the back end of the probe 10 so that the probe 10 can be fitted in the fore end part of the holder 11. A laser light reflecting layer 12 such as a gold plate layer is provided on the inner surface of the tapered fore end part of the holder 11. A lead wire 13 is provided for detecting a temperature. The laser light irradiation apparatus of this second embodiment is mainly suitable for the irradiation against the skin layer of a human body.

In the present invention, since the probe is fabricated from the synthetic resin material, rather than a ceramic material, it is much easier to mould the material to be a desired shape. Therefore, as shown in the third embodiment of FIG. 6, the material can be mold to be a probe 10A having an elaborate shape suitable for, for example, a treatment for uterine cancers formed adjacent to the cervical os of an uterine U.

Figure 6:
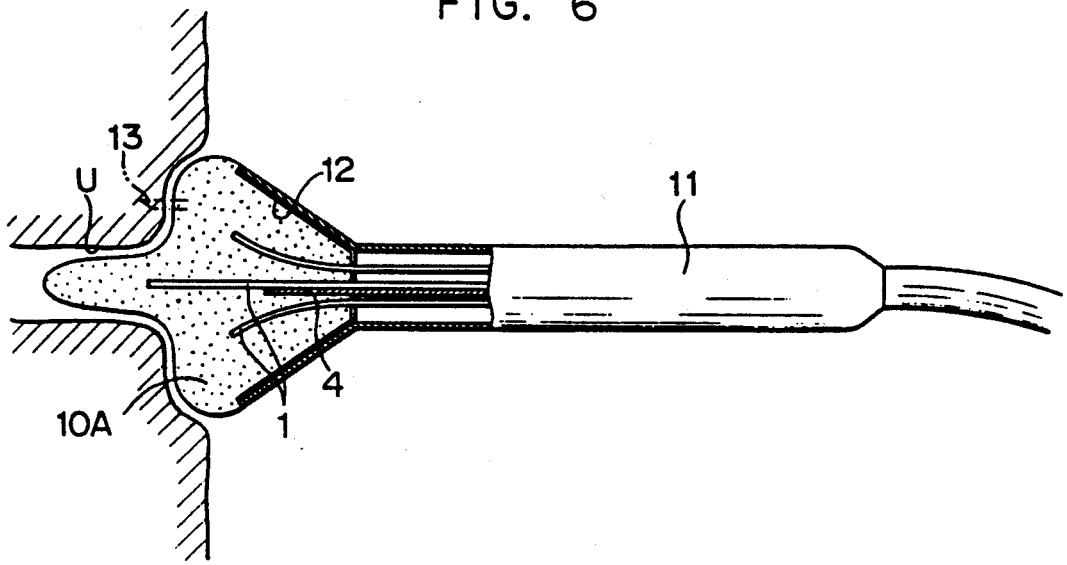
FIG. 6 is a longitudinal sectional view of an irradiation apparatus in a third embodiment.
Figure 7:
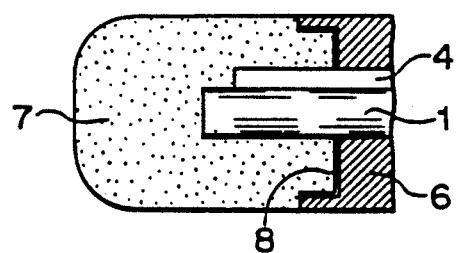
FIG. 7 is a longitudinal sectional view of an important part of an irradiation apparatus in a fourth embodiment.

In FIG. 6 showing the third embodiment and FIG. 7 showing the fourth embodiment, each lead wire 4 for detecting the temperature done not project from the external surface of the fore end portion of the probe 10A or a probe 7. That is to say, each fore end portion of each lead wire remains buried in the synthetic material of the probe 10A or the probe 7. In this case, if the relation of the temperature in the treated tissues and the temperature in the probe 10A or the probe 7 is known, the temperature of the tissues can be controlled by detecting the temperature in the probe 10A or in the probe 7, although accuracy in controlling is decreased to some degree.

Figure 8:
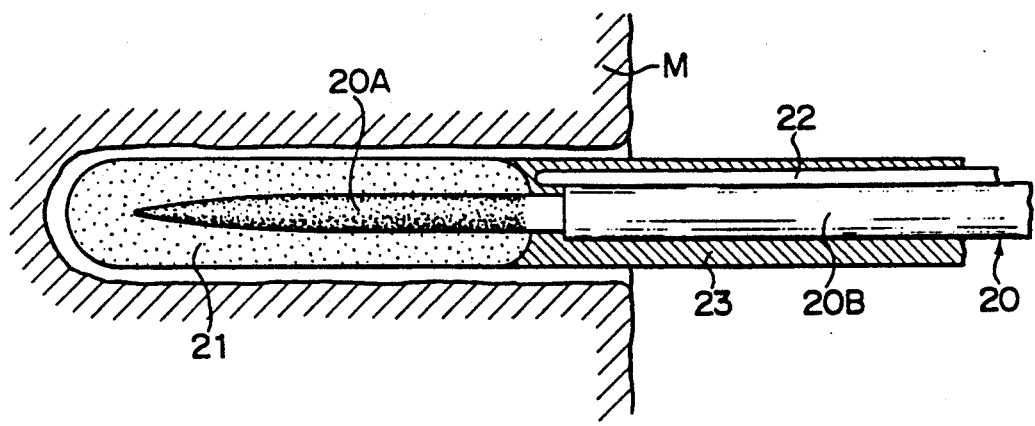
FIG. 8 is a longitudinal sectional view of an important part of an irradiation apparatus in a fifth embodiment.

FIG. 8 shows the fifth embodiment. In this embodiment, an apparatus is used effectively in a treatment not for the surface of tissues, but for inside of the tissues. At the fore end portion of an optical fiber 20, a clad 20B is removed so that a core 20A is exposed. The tip end of the core 20A is tapered. A laser light scattering layer is formed on almost all of the external surface of the core 20A. In this figure, this laser light scattering light is indicated by marking dots. For forming this scattering layer, first, ceramic powders such as silicon dioxide and the like are sprayed and heated to a temperature which is slightly lower than its melting point. Therefore, the original sprayed powders do not become to be homogeneous due to incomplete heating. Then, these incompletely heated ceramic powders are cooled. Accordingly, the laser light scattering layer can be formed on the core 20A, where the powders partly melt and fuses and partly remain in a particle state. Due to this scattering layer, when the laser light is emitted from the external surface of the core 20A, the laser light impinges on each resulting ceramic powder with refraction to be scattered.

On the other hand, a probe 21 is provided so as to surround the core 20A covered with this scattering layer. The probe 21 is fabricated from a synthetic material containing scattering particles in the same manner as the first embodiment.

The external surface of a lead wire 22 detecting a temperature is gold plated. Then, the fore end of the lead wire 22 fixed to the optical fiber 20 and located adjacent to the back end of the probe 21. The lead wire 22 together with the optical fiber 20 is surrounded by a flexible sheath 23 fabricated from synthetic resin such as polyethylene, urethane and the like, silicone rubber and so on. By moulding, the sheath 23 is fixed integrally to the lead wire 22, the optical fiber 20 and the probe 21.

Figure 9:
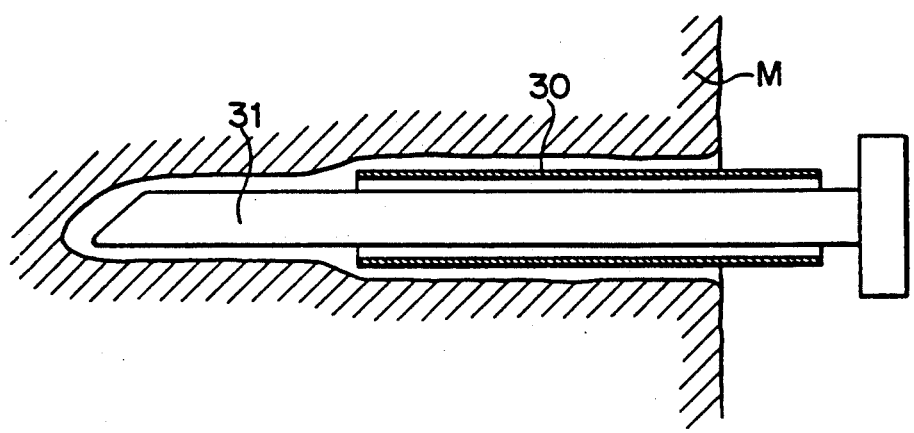
FIG. 9 is a longitudinal sectional view showing an embodiment of forming a guide in the tissues prior to inserting of the apparatus of FIG. 8.

In case of applying this apparatus of the fifth embodiment, as shown in FIG. 9, first, a so-called puncture needle 31 together with a guide tube 30 is inserted into the tissues M such as lever tissues. Next, only the puncture needle 31 is removed. Then, instead of the needle 31, the fore end portion of this laser light irradiation apparatus is inserted into the tissues M so as to go through the guide tube 30. Then, the laser light is fed into the optical fiber 20 to be emitted from the core 20A provided at the fore end portion of the optical fiber 20. The laser light is scattered in the scattering layer covering the core 20A. Then, the scattered and emitted laser light is fed into the probe 21 and goes through it, while the laser light is repeatedly scattered by the scattering particles in the probe 21. At last, the laser light is emitted from the external surface of the probe 21 uniformly. This apparatus is applied for a local thermal therapy for cancer tissues in a liver, encephalic malignant tumors and cancer tissues in a breast.

The scattering particles contained in the scattering layer are in principle the same as the above mentioned scattering particles in the probe. However, the particles, which cannot make a film when they melt, are not suitable, thus, ceramic particles are generally used for the scattering particles.

Further, if desired, a surface layer might be formed on each surface of the above mentioned several kinds of probes or the above mentioned scattering surface layer covered on the core 20A to give a high scattering effect. This surface layer contains the light scattering particles, which have the larger refractive index than that of the material of the probe or the above mentioned synthetic material, such as sapphire, silicon dioxide, aluminum oxide and the like, the laser light absorbing particles, which can be included in the probe as described before, such as carbon and the like and a binder, which sticks the particles to each surface and forms a film on the surface as described hereinafter.

The laser light is scattered by the light scattering particles, further, when the laser light impinges on the laser light absorbing particles, the greater part of the energy of the laser light is converted to heat energy.

By doing so, as the vaporization of the tissues is accelerated, the tissues can be incised with a low energy of the laser light penetrated into the probe. Therefore, when the tissues are incised, the probe can be moved rapidly. Further, since the required energy of the laser light penetrating into the probe is low, the medical operation can be carried in short time with a cheap and small scaled laser light generator.

On the other hand, referring to the surface layer, if a dispersion containing the laser light absorbing particles and the light scattering particles is coated on the surface of the probe, after a vaporization of a dispersion medium, the contact of the probe having the surface layer with the tissues or other substances causes a damage to the surface layer, because the both kinds of particles are attached to the surface of the probe only by physical adsorptive power.

The binder secures the laser light absorbing particles and the light scattering particles to the surface of the probe and enhances adhesion of the surface layer to the probe. In this case, the binder is preferably made of light penetrating particles such as synthetic particles or ceramic particles such as quartz particles and the like. For forming the film, when the synthetic particles are used as the material of the binder, the particles should be melted, or when the ceramic particles having a higher melting point than that of the probe are used, the surface of the probe should be melted.

Further, by forming a rough surface on the surface of the probe or by forming the above mentioned surface layer on the rough surface, the laser light can be irradiated more effectively, because, the laser light is scattered on the rough surface when the laser light is emitted. If desired, the rough surface is formed on the core 20A, further the above mentioned scattering layer might be formed on the rough surface.

Although, in each embodiment described hereinbefore, the fore end of the optical fiber is buried in the synthetic material of the probe, the fore end of the optical fiber might be located so as to be apart from the back end of the probe. However, an exception is the embodiment of FIG. 8, because the scattering layer in this embodiment is formed on the surface of the core and the probe is set to be provided so as to surround the core. Then, in case of providing a gap between the fore end of the optical fiber and the back end of the probe of the present invention other than the probe in the embodiment of FIG. 8, impurities such as dusts and the like are produced in the gap; further, the impurities are attached to the surfaces of the back end of the probe and the fore end of the optical fiber or fibers. Accordingly, since the laser light is impinged on the impurities, the surfaces of the back end of the probe are heated. That is to say, the power level of the laser light fed into the probe is lowered. Therefore, the fore end of the optical fiber is preferably buried in the synthetic material of the probe.

While preferred embodiments have been described, it is apparent that the present invention is not limited to the specific embodiments thereof.

What is claimed is:

1. A laser light irradiation apparatus comprising:
   a light emitting member formed of a molded laser light transmissive synthetic resin;
   light scattering particles dispersed throughout said synthetic resin, wherein the light scattering particles have a larger refractive index than that of the synthetic resin;
   at least one transmitting member, through which laser light is transmitted so as to be applied to said light emitting member, wherein said laser light transmitting member is an optical fiber and a fore end portion of a core of said optical fiber is embedded in the synthetic resin of said light emitting member; and
   a laser light scattering layer formed on the surface of the embedded part of said core, said laser light scattering layer being fabricated from heat resistant ceramic particles, a portion of which are fused together and a portion of which remain in a particle state.

2. A laser light irradiation apparatus comprising:
   a light emitting member formed of a molded laser light transmissive synthetic resin;
   light scattering particles dispersed throughout said synthetic resin, wherein the light scattering particles have a larger refractive index than that of the synthetic resin;
   at least one transmitting member, through which laser light is transmitted so as to be applied to said light emitting member;
   a holder, wherein said light emitting member is held and surrounded by a fore end portion of said holder; and
   a laser light reflecting layer covering at least a part of an inner surface of said holder, said inner surface contacting said light emitting member.

3. An apparatus according to claim 2, wherein said reflecting layer is a gold plated layer.

4. A laser light irradiation apparatus comprising:
   a light emitting member formed of a molded laser light transmissive synthetic resin;
   light scattering particles dispersed throughout said synthetic resin, wherein the light scattering particles have a larger refractive index than that of the synthetic resin;
   at least one transmitting member, through which laser light is transmitted so as to be applied to said light emitting member; and
   a lead wire means for detecting a temperature, which is inserted through said light emitting member so as to project from a light emitting surface of the fore end portion of said light emitting member, wherein a part of said lead wire which passes through the light emitting member is embedded in the synthetic resin of said light emitting member.

5. An apparatus according to claim 4 wherein at least the embedded inserting part and the projecting part of said lead wire are coated with a laser light reflecting material.

6. An apparatus according to claim 1 wherein a rough surface is formed on the surface of said light emitting member.

7. An apparatus according to claim 4, wherein the synthetic resin is a thermoplastic synthetic resin.

8. An apparatus according to claim 1, wherein the synthetic resin is selected from the group consisting of: silicone resin, acrylic resin, carbonate resin, polyamide resin, polyethylene resin, urethane resin and polyester resin.

9. An apparatus according to claim 1, wherein the light scattering particles are selected from the group consisting of: diamond particles, sapphire particles, quartz particles, single crystal zirconium oxide particles, particles of transmissible and heat resistant synthetic resins, laser light reflective metal particles, and particles on which laser light reflective metals have been coated.

10. An apparatus according to claim 4, wherein the synthetic resin is a thermoplastic synthetic resin.

11. An apparatus according to claim 4, wherein the synthetic resin is selected from the group consisting of: silicone resin, acrylic resin, carbonate resin, polyamide resin, polyethylene resin, urethane resin and polyester resin.

12. An apparatus according to claim 4, wherein the light scattering particles are selected from the group consisting of: diamond particles, sapphire particles, quartz particles, single crystal zirconium oxide particles, particles of transmissible and heat resistant synthetic resins, laser light reflective metal particles, and particles on which laser light reflective metals have been coated.

13. An apparatus according to claim 4, wherein the projecting part of the lead wire for sensing temperature comprises a thermocouple.

* * * * *